United States Patent [19]

McIver et al.

[11] Patent Number: 5,126,274

[45] Date of Patent: Jun. 30, 1992

[54] METHOD AND APPARATUS FOR MEASURING DIAMONDOID COMPOUND CONCENTRATION IN HYDROCARBONACEOUS GAS STREAMS

[75] Inventors: George E. McIver; Robert E. Roach, both of Dallas, Tex.

[73] Assignee: Mobil Oil Corporation, Fairfax, Va.

[21] Appl. No.: 489,112

[22] Filed: Mar. 6, 1990

[51] Int. Cl.⁵ .................. G01N 5/00; G01N 11/00; G01N 31/02; G01N 33/00

[52] U.S. Cl. .................. 436/140; 422/62; 422/83; 422/88; 422/93; 436/50; 436/52; 436/55; 436/178; 436/181; 436/908; 585/803

[58] Field of Search .......... 585/803; 436/139, 140, 436/177, 50, 52, 55, 178, 181, 908; 422/62, 83, 88, 93

[56] References Cited

U.S. PATENT DOCUMENTS

| | | | |
|---|---|---|---|
| 4,952,747 | 8/1990 | Alexander et al. | 585/803 |
| 4,952,748 | 8/1990 | Alexander et al. | 585/803 |
| 4,952,749 | 8/1990 | Alexander et al. | 585/803 |
| 4,982,049 | 1/1991 | Alexander et al. | 585/803 |
| 5,019,665 | 5/1991 | Partridge et al. | 585/803 |

OTHER PUBLICATIONS

"Carbon Disulfide", The Merck Index, 10th Ed., Merck & Co., Inc, ©1983, p. 251.

Fort, Jr., R. C., The Chemistry of Diamond Molecules, Marcel Dekker, 1976.

King, W. J., "Operating Problems in the Hanlan Swan Hills Gas Field", Society of Petroleum Engineers, SPE Gas Technology Symposium, Dallas, Tex., Jun. 1968.

Primary Examiner—Robert J. Hill, Jr.
Attorney, Agent, or Firm—Alexander J. McKillop; Charles J. Speciale; Robert B. Furr, Jr.

[57] ABSTRACT

The diamondoid compound content of a hydrocarbon gas sample stream is measured in a process and apparatus for the controlled precipitation and collection of diamondoid compounds.

9 Claims, 2 Drawing Sheets

METHOD AND APPARATUS FOR MEASURING DIAMONDOID COMPOUND CONCENTRATION IN HYDROCARBONACEOUS GAS STREAMS

BACKGROUND OF THE INVENTION

This invention relates to the controlled removal of certain components from hydrocarbon streams. It more particularly refers to separating diamondoid organic compounds from hydrocarbon streams containing such, and to precipitating these diamondoid compounds in a manner which facilitates their subsequent analysis. Still more particularly, the invention relates to a method and apparatus for determining the diamondoid content of a natural gas stream.

Many hydrocarbonaceous mineral streams contain some small proportion of diamondoid compounds. These high boiling, saturated, three-dimensional polycyclic organics are illustrated by adamantane, diamantane, triamantane and various side chain substituted homologues particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment. For a survey of the chemistry of diamondoid compounds, see Fort, Jr., Raymond C., *The Chemistry of Diamond Molecules*, Marcel Dekker, 1976.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, not these compounds represent both a larger problem and a larger opportunity. The presense of diamondoid compounds in natural gas has been found to cause plugging in the process equipment requiring costly maintenance downtime to remove. On the other hand, these very compounds which can deleteriously affect the profitability of natural gas production are themselves valuable products.

SUMMARY OF THE INVENTION

The present invention provides a method and apparatus for determining the relative content of diamondoid compounds in a hydrocarbon gas stream.

In its method aspects, the invention comprises the steps of:
(a) providing a gaseous hydrocarbon sample stream at a pressure above atmospheric;
(b) depressuring and heating said gaseous hydrocarbon stream to a temperature sufficient to prevent precipitation of diamondoid compounds;
(c) separating liquid components from said depressured gas stream of step (b) to provide a first overhead gaseous stream substantially free of liquid and a first liquid bottom stream;
(d) providing a tubular conduit in contact with a cooling medium;
(e) passing said first overhead gaseous stream of step (c) through said tubular conduit of step (d) thereby cooling said gaseous hydrocarbon stream and precipitating at least a portion of said diamondoid compounds contained in said gaseous hydrocarbon sample stream;
(f) withdrawing a chilled stream from said tubular conduit;
(g) separating liquid components from said chilled stream of step (e) to provide a second overhead gaseous stream substantially free of liquid and a second liquid bottom stream;
(h) contacting said second overhead gaseous stream with a sorbent in a sorption zone for a period of time sufficient for said sorbent to remove substantially all of the diamondoid compounds remaining in said second overhead gaseous stream;
(i) withdrawing a stream of substantially dry hydrocarbon gas from said sorption zone;
(j) collecting said first liquid bottom stream of step (c) and said second liquid bottom stream of step (g);
(k) monitoring the pressure drop across said tubular
(l) monitoring the pressure drop across said sorption zone of step (h);
(m) interrupting the flow of said gaseous hydrocarbon sample stream when said pressure drop across either of said tubular conduit of step (d) or said sorption zone of step (h) indicate plugging;
(k) removing precipitated diamondoid compounds from said tubular conduit of step (d) and said sorbent of step (h).

The invention further comprises an apparatus for determining the content of diamondoid compounds in a gaseous hydrocarbon stream comprising:
(a) sampling means for providing a gaseous hydrocarbon sample stream at a pressure above atmospheric;
(b) means for depressuring and heating said gaseous hydrocarbon stream to a temperature sufficient to prevent precipitation of diamondoid compounds;
(c) first means for separating liquid components from said depressured gas stream to provide a first overhead gaseous stream substantially free of liquid and a first liquid bottom stream:
(d) a tubular conduit in contact with a cooling medium, said tubular conduit in communication with said separation means (c);
(e) conduit means for passing said first overhead gaseous stream from said first separation means (c) through said tubular conduit (d) whereby said gaseous hydrocarbon stream is cooled and at least a portion of said diamondoid compounds contained in said gaseous hydrocarbon sample stream is precipitated;
(f) means for withdrawing a chilled stream from said conduit means (e);
(g) second means for separating liquid components from said withdrawn chilled stream to provide a second overhead gaseous stream substantially free of liquid and a second liquid bottom stream;
(h) a sorption vessel in valved communication with said second separation means (g) for contacting said second overhead gaseous stream with a sorbent in for a period of time sufficient for said sorbent to remove substantially all of the diamondoid compounds remaining in said second overhead gaseous stream;
(i) conduit means for withdrawing a stream of substantially dry hydrocarbon gas from said sorption zone;
(j) a first vessel for collecting said first liquid bottom stream from said first separation means (c);

(k) a second vessel for collecting said second liquid bottom stream from said second separation means (g);

(k) means for monitoring the pressure drop across said tubular conduit (d);

(l) means for monitoring the pressure drop across said sorption zone (h); and (m) valve means for interrupting the flow of said gaseous hydrocarbon sample stream when said pressure drop across either of said tubular conduit (d) or said sorption zone (h) indicate plugging.

DETAILED DESCRIPTION

Figure 1:
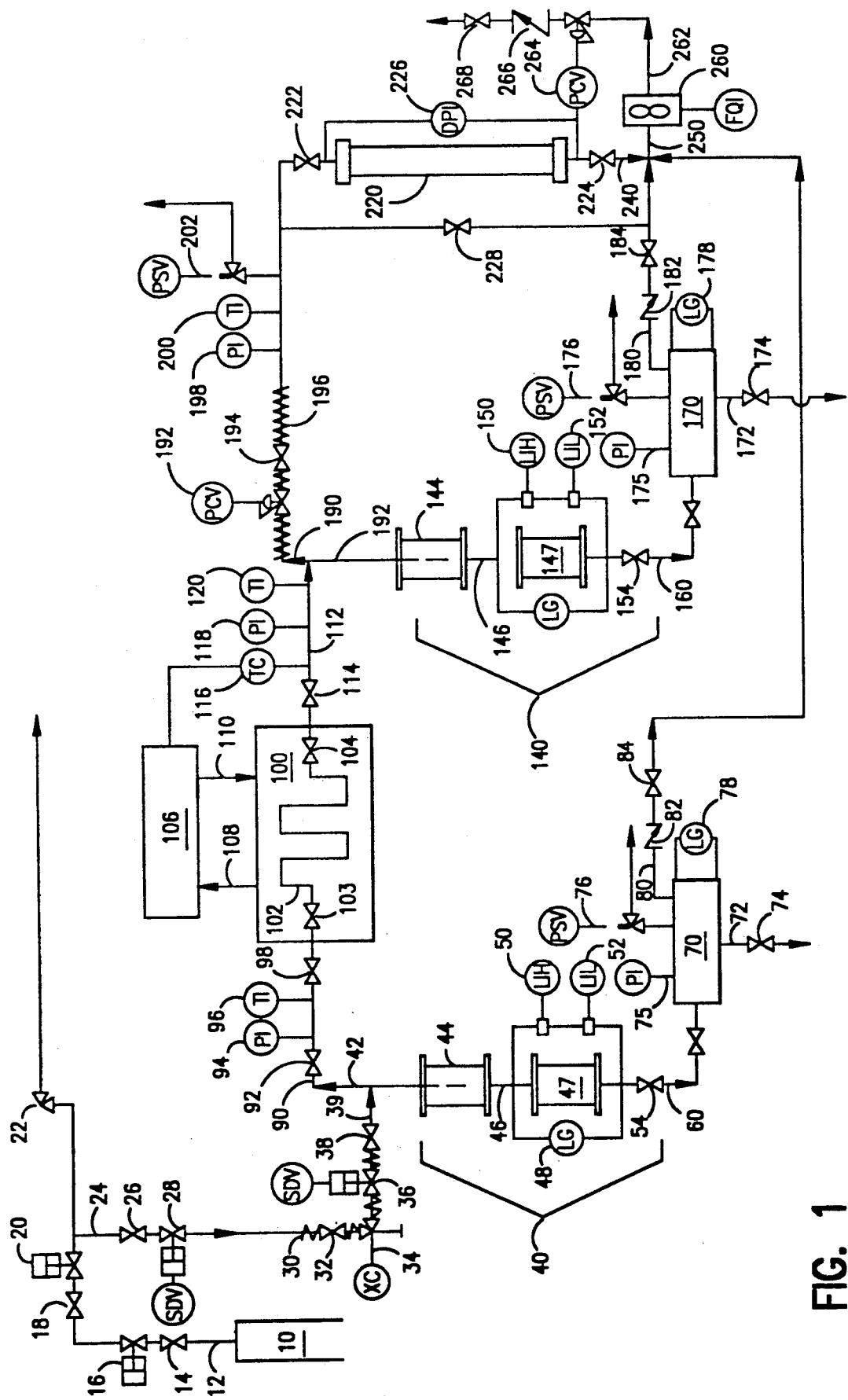
FIG. 1 is a simplified schematic representation of an apparatus suitable for carrying out the essential processing steps of the present invention.

Referring now to FIG. 1, a preferred embodiment of the present invention is schematically illustrated. For the purposes of this disclosure, the term "diamondoid analyzer" refers to the equipment shown in the flow scheme of FIG. 1 beginning with and downstream of sample line 24.

A natural gas stream is withdrawn from wellhead 10 through line 12 at high pressure, generally from about 2,000 psig to about 15,000 psig, most typically around 6,000 psig. The temperature of the withdrawn natural gas stream generally ranges from about 200° F. to about 260° F. and is most typically about 240° F. Line 12 is typically equipped with block valves 14 and 18 as well as remotely controlled shutdown valves 16 and 20. Flow control valve 22, commonly referred to as a choke, reduces the natural gas pressure downstream of the choke to between about 900 and about 1400 psig.

Sample line 24 draws off a portion of the high pressure natural gas from line 12 for determination of the diamondoid compound content. Line 24 is equipped with block valves 26 and 32 and shutdown valves 28 and 36. Shutdown valve 36 preferably functions as an overpressure safety shutdown, interrupting flow to the diamondoid analyzer if pressure downstream of control valve exceeds about 1400 psig.

The high pressure natural gas sample stream is depressured across flow control valve 34 to a pressure of from about 900 to about 1400 psig, typically about 1200 psig. Line 24 is preferably heat traced with steam or electric heat tracing 30 from a point upstream of block valve 32 downstream to the inlet of block valve 38.

Heat tracing maintains the sample stream at a temperature sufficient to prevent substantial precipitation of diamondoid compounds. Temperature within the transfer tubing such as line 24 is closely controlled to prevent icing and/or diamondoid compound deposition in the transfer tubing and to concentrate substantially all of the diamondoid compounds precipitated from the natural gas stream in the heat exchange tube 102 and the dessicant tower 220. This facilitates measurement of the total diamondoid content of the sampled stream for evaluation of the natural gas well under consideration.

To illustrate solubility and to exemplify naturally occuring diamondoid concentrations, adamantane, diamantane, and triamantane, the diamondoid compound concentrations most commonly found in natural gas streams, remain dissolved in a typical natural gas stream at 1200 psig and 200° F. However, it can well be seen that such concentrations vary and the particular process conditions for the testing procedure of the present invention may be varied by those of ordinary skill in the art with a reasonable amount of trial and error to tailor the process conditions to the particular natural gas stream under consideration. For example higher diamondoid concentrations would likely require higher transfer line temperatures to restrict precipitation of diamondoid compounds to the heat exchange tube 102 and the dessicant tower 220.

Following the depressurization step, the natural gas sample stream is charged to a primary vapor/liquid separator 40. The particular configuration of the primary vapor/liquid separator is not critical and may comprise any suitable vessel which provides effective segregation of the overhead vapor stream from the liquid bottom stream. The separator vessel may contain trays, e.g., sieve trays, or packing, e.g., Berl saddles. Alternatively, the separator may comprise a single stage separation vessel equipped with a vapor disengaging pad. In the most preferred embodiment, however, the vapor/liquid separator comprises two stacked vessels fed through an annular tee 42. This preferred vapor/liquid separator is shown in greater detail in FIG. 2.

Figure 2:
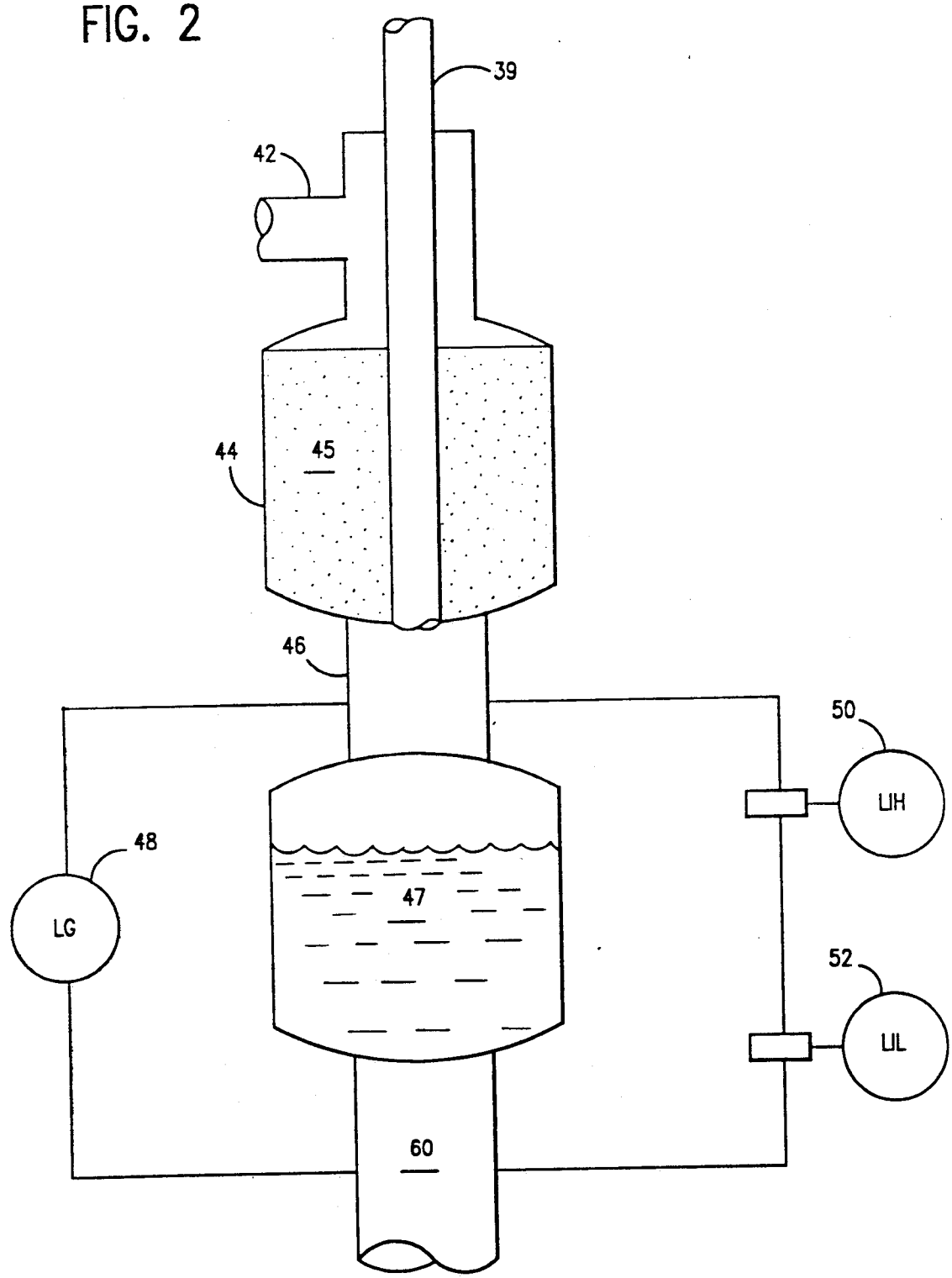
FIG. 2 is a simplified diagram detailing the preferred gas-liquid separator for use in one embodiment of the present invention.

Referring now to FIG. 2, line 39 extends through annular tee 42 and enters the upper separation vessel 44. Annular tee 42 is preferably assembled from Swagelok brand tube fittings. Vessel 44 is preferably a Welker brand flanged-head sample cylinder having a capacity of approximately 1 gallon, manufactured by the Welker Engineering Company of Sugarland, Tex. Due to the potentially corrosive nature of the natural gas sample, the Welker cylinder may be constructed of nickel-containing alloys such as Hastelloy brand or Monel brand alloys, or may alternatively be constructed of carbon steel lined with nickel-rich alloy for corrosion resistance. The upper Welker cylinder contains packing, preferably $\frac{1}{4}$ inch Raschig rings. Line 39 extends downward through the packing to a point near the bottom of the upper Welker cylinder. The inner diameter of transfer line 46 is sufficiently small that the $\frac{1}{4}$ inch Raschig rings are retained within the upper Welker cylinder.

The vapor/liquid mixture flows out of line 39, upward through the Raschig rings. The lower separation vessel is also preferably a Welker brand flanged-head sample cylinder, alloyed as described above. The lower vessel 47 acts as a liquid collection reservoir and is fitted with level gauge 48 as well as high level indicator 50 and low level indicator 52. During process operation, manual valve 54 (shown in FIG. 1) is set to maintain liquid level in the lower cylinder between the high and low indicators, 50 and 52, respectively. Liquid flows out of the lower vessel 47 via line 60.

Referring again to FIG. 1, the liquid bottom stream from vapor/liquid separator 40 is withdrawn through line 60 and enters primary accumulator drum 70. The primary accumulator drum may comprise any suitable closed pressure vessel alloyed to resist attack from sour ($H_2S$-containing) liquid and vapor. A preferred example of such a vessel is a 16 gallon A-P-C pressure vessel rated for 130 psig at 200° F., fabricated from 316 alloy and commercially available from Alloy Products Corporation of Waukesha, Wis. The liquid is typically retained within the drum for the duration of the test run. However, it is to be understood that if the concentration of diamondoid compounds were significantly lower and the liquid concentrations were significantly higher, a liquid draw-off line such as line 72, equipped with ball valve 74 could optionally be installed to avoid the necessity of breaking tubing connections during the test run. Liquid drawn off during the sample run may be stored in a sample bomb for subsequent laboratory analysis. Primary accumulator drum 70 is preferably fitted with a pressure indicator 75, pressure relief valve 76, and level gauge 78. Vapor from primary accumulator 70 is drawn off through line 80 which is equipped with check valve 82 and shutoff valve 84.

The overhead vapor stream from primary vapor/liquid separator 40 flows upward through annular tee 42 and enters line 90 which includes block valves 92 and 98 as well as pressure indicator 94 and temperature indicator 96. As the overhead vapor stream from separator 40 flows into gas cooler 100, the vapor stream is most preferably at a temperature just above the saturation temperature of the diamondoid compounds in the natural gas. Gas cooler 100 contains at least one heat exchange tube 102 which is in contact with a chilled heat transfer solution. While a single heat exchange tube is shown, it is to be understood that a plurality of heat exchange tubes in series or parallel may be employed. The heat exchange tube 102 preferably includes ball valves 103 and 104. Tube 102 is preferably immersed in an aqueous solution of ethylene glycol which continuously circulates through chiller 106 through lines 108 and 110. Diamondoid compounds precipitate from the vapor stream and deposit on the inner walls of tube 102. For this reason, it is most preferred to fabricate the heat exchange tube bends from Swagelok brand tubing elbows and bends ("U" joints) to facilitate cleaning of the heat exchange tube assembly following shutdown.

The vapor stream is then withdrawn from cooler 100 through line 112 which includes ball valve 11;. Temperature controller 116 measures the temperature of the vapor effluent in line 112 and adjusts the temperature of the chilled heat transfer solution to attain an effluent temperature of from about 60° to 120° F., preferably about 100° F. The chiller may be any suitable type of the many commonly available in the industry. However, the most preferred chiller for use in conjunction with the present invention is the Mydax brand air cooled chiller, available from Mydax, Incorporated of Auburn, Calif.

The vapor effluent from cooler 100 flows through line 112 to secondary vapor/liquid separator 140, which is preferably similar in configuration to the primary upstream vapor/liquid separator 40. As is the case with primary vapor/liquid separator 40, the particular configuration of the secondary vapor/liquid separator 140 is not critical and may suitably comprise any of the vapor/liquid separation equipment types described above, but most preferably comprises two (2) stacked Welker sample cylinders, with the upper cylinder containing Raschig rings, also as described above.

Liquid is withdrawn from the lower cylinder 147 through line 160 which is fitted with valve 154 to regulate liquid level within the secondary separator and enters secondary liquid accumulator drum 170. The secondary accumulator drum may comprise any suitable closed pressure vessel alloyed to resist attack from sour ($H_2S$-containing) liquid and vapor. The preferred vessel may be identical to that used for the primary accumulator drum, i.e., a 16 gallon A-P-C pressure vessel rated for 130 psig at 100° F., fabricated from 316 alloy and commercially available from Alloy Products Corporation of Waukesha, Wis.

The liquid is typically retained within the drum for the duration of the test run. However, it is to be understood that if the concentration of diamondoid compounds were significantly lower and the liquid concentrations were significantly higher, a liquid draw-off line such as line 172, equipped with ball valve 174 could optionally be installed to avoid the necessity of breaking tubing connections during the test run. Primary accumulator drum 170 is preferably fitted with a pressure indicator 175, pressure relief valve 176, and level gauge 178. Vapor from primary accumulator 170 flows overhead through line 180 which is equipped with check valve 182 and shutoff valve 184.

The overhead vapor stream from secondary vapor/liquid separator 140 flows upward through annular tee 142 and enters line 190 which includes pressure control valve 192 and block valve 194 as well as pressure indicator 198 and temperature indicator 200. Line 190 is preferably equipped with pressure relief valve 202 which vents to a low pressure flare line (not shown). The pressure control valve 192 decreases line pressure from around 1200 psig to about 40 psig. To avoid icing and/or hydrate formation due to Joule-Thompson cooling across the pressure control valve, the temperature of line 190 is regulated to between about 100° and 140° F., typically about 120° F. with steam or electric heat tracing 196.

To remove any remaining diamondoid compounds, liquid hydrocarbons, or water from the natural gas stream, the vapor stream from line 190 is then charged to a dessicant tower 220. The dessicant tower 220 includes shutoff valves 222 and 224 at its inlet and outlet, respectively. Differential pressure indicator 226 measures the pressure drop across dessicant tower 220. Closing shutoff valves 222 and 224 and opening valved bypass line 228 allows dessicant tower 220 to be removed during process operation for maintenance dessicant replacement or regeneration. However, it is to be understood that if dessicant tower 220 is removed during process operation, the removed contents of the dessicant tower should be retained in a closed vessel for subsequent laboratory analysis.

Gas flow through lines 80 and 180 together with dry gas effluent from dessicant tower 220 flow through line 250 and enter flowmeter 260, which is preferably equipped with a flow totalizer. In other words, flowmeter 260 preferably measures not only instantaneous flow but also records the total flow through the flowmeter over a set period of time. Numerous flow instruments currently available and well known to those skilled in the art fulfill this requirement, however, a particularly preferred flow instrument is the Sponster model flowmeter, manufactured by the Sponster company of Westminster, S.C.

Gas effluent from flowmeter 260 flows through line 262 and pressure control valve 264 which regulates upstream pressure at or below about 35 psig. The depressured natural gas then flows through check valve 266 and shutoff valve 268 and is exhausted from the analyzer system to a low pressure flare line (not shown).

ANALYZER OPERATION

The analyzer system is typically skid mounted so that it may be easily transported to the well site. Before the test run, the diamondoid analyzer is thoroughly rinsed with solvent in which diamondoids are readily soluble, for example, carbon disulphide. The heat exchange tube 102 from cooler 100 is removed from the diamondoid analyzer, disassembled, rinsed, and visually inspected to assure that no diamondoid deposits remain within the tube. Thus it is most preferred to fabricate the heat exchange tube bends from Swagelok brand tubing elbows to facilitate cleaning of the heat exchange tube assembly.

Similarly, the dessicant tower is removed from the diamondoid analyzer and rinsed with solvent to dissolve any residual diamondoid deposits. For this reason, it is preferred to fabricate the dessicant tower vessel with removeable heads. A particularly preferred example of such a vessel is assembled from 316 stainless steel pipe and fittings.

To test a selected well for diamondoid compound content, line 24 is teed into the high pressure well outlet line 12. The natural gas sample is drawn through the diamondoid analyzer at a rate of about 30,000 SCF/day. The test duration is a function of the diamondoid content in the natural gas stream, and typical test runs take between about 6 and about 18 hours. The actual time for the test is determined by pressure drops across the gas cooler 100 and the dessicant tower 226. Process temperatures are controlled as noted above such that essentially all of the diamondoid compounds contained in the natural gas stream precipitate out and are deposited in the heat exchange tube 102 of gas cooler 100 and in the dessicant tower 220. Gas pressure drops approximately 5 psi across the gas cooler at startup. As diamondoid solids deposit inside the heat exchange tube 102, the pressure drop gradually increases. Similarly, the pressure drop across the dessicant tower 220 is about 5 psi at startup. At a pressure drop of 150 psi, the heat exchange tube is nearly plugged, and at a pressure drop of 35 psi, the sorbent in the dessicant tower may be damaged. Thus when the pressure drop across the gas cooler reaches 150 psi or the pressure drop across the dessicant tower reaches 35 psi, block valve 26 and shutdown valve 28 are closed. The total gas flow through flowmeter 260 is recorded and the diamondoid analyzer is taken off stream.

The skid-mounted diamondoid analyzer is then transported to a laboratory facility and disassembled. The solids deposited in the heat exchange tube 102 and the dessicant tower 220 are removed, weighed, and analyzed in the laboratory.

Liquid hydrocarbons and trace amounts of water are collected in primary and secondary accumulators 70 and 170. These vessels are emptied and the accumulated liquid composition and mass are recorded.

The diamondoid compound content of the natural gas stream is then calculated as a weight percent of the total natural gas flowrate by dividing the mass of the collected diamondoid compounds by the sum of the masses of the collected liquid from accumulators 70 and 170 together with the dry gas as measured by flowmeter 260.

Changes and modifications in the specifically described embodiments can be carried out without departing from the scope of the invention which is intended to be limited only by the scope of the appended claims.

What is claimed is:

1. A method for detecting diamondoid compounds in a gaseous hydrocarbon stream comprising the steps of:
   (a) providing a gaseous hydrocarbon sample stream at a pressure above atmospheric;
   (b) depressuring and heating said gaseous hydrocarbon sample stream to a temperature sufficient to prevent precipitation of diamondoid compounds;
   (c) separating liquid components from said depressured and heated gaseous hydrocarbon sample stream of step (b) to provide a first overhead gaseous stream substantially free of liquid and a first liquid bottom stream;
   (d) providing a tubular conduit in contact with a cooling medium;
   (e) passing said first overhead gaseous stream of step (c) through said tubular conduit of step (d) thereby cooling said first overhead gaseous stream and precipitating at least a portion of diamondoid compounds contained in said first overhead gaseous stream;
   (f) withdrawing a chilled stream from said tubular conduit;
   (g) separating liquid components from said chilled stream of step (f) to provide a second overhead gaseous stream substantially free of liquid and a second liquid bottom stream;
   (h) contacting said second overhead gaseous stream with a sorbent in a sorption zone for a period of time sufficient for said sorbent to remove substantially all diamondoid compounds remaining in said second overhead gaseous stream;
   (i) withdrawing a stream of substantially dry hydrocarbon gas from said sorption zone;
   (j) collecting said first liquid bottom stream of step (c) and said second liquid bottom stream of step (g);
   (k) monitoring the pressure drop across said tubular conduit of step (d);
   (l) monitoring the pressure drop across said sorption zone of step (h);
   (m) interrupting the flow of said gaseous hydrocarbon sample stream when said pressure drop across either of said tubular conduit of step (d) or said sorption zone of step (h) indicate plugging;
   (n) removing precipitated diamondoid compounds from said tubular conduit of step (d) and said sorbent of step (h).

2. The process of claim 1 further comprising
   (i) measuring the mass of said collected first and second liquid bottom streams;
   (ii) measuring the mass of diamondoid compounds precipitated in said tubular conduit;
   (iii) measuring the mass of diamondoid compounds sorbed in said sorption zone;
   (iv) measuring the mass of said dry hydrocarbon gas withdrawn in step (i); and
   (v) determining the diamondoid compound content of said gaseous hydrocarbon stream as the quotient of the sum of the masses measured in step (ii) and (iii) divided by the sum of the masses measured in steps (i) and (iv).

3. The process of claim 1 wherein said separating step (c) further comprises flowing said depressured and heated gaseous hydrocarbon sample stream of step (b) through a packed bed gas/liquid separation zone.

4. The process of claim 3 wherein said packed bed gas/liquid separation zone contains Raschig rings.

5. The process of claim 1 wherein said separating step (g) further comprises flowing said chilled stream of step (f) through a packed bed gas/liquid separation zone.

6. The process of claim 5 wherein said packed bed gas/liquid separation zone contains Raschig rings.

7. The process of claim 1 wherein said precipitated diamondoid compound removal step (n) further comprises dissolving diamondoid compounds in a solvent.

8. The process of claim 7 wherein said solvent is carbon disulfide.

9. An apparatus for detecting diamondoid compounds in a gaseous hydrocarbon stream comprising:

(a) sampling means for providing a gaseous hydrocarbon sample stream at a pressure above atmospheric;

(b) means for depressuring and heating said gaseous hydrocarbon sample stream to a temperature sufficient to prevent precipitation of diamondoid compounds said depressuring and heating means in communication with said sampling means;

(c) first means for separating liquid components from a depressured and heated gaseous hydrocarbon sample stream from said depressing and heating means (b) said first separation means being downstream from and in communication with said depressuring and heat means (b) to provide a first overhead gaseous stream substantially free of liquid and a first liquid bottom stream said first separation means comprising a separation zone having an upper packed bed zone superimposed above a lower liquid collection zone and a feed conduit entering said separation zone above said packed bed zone and extending downwardly through said packed bed zone to retain packing in said upper packed bed zone;

(d) a tubular conduit in contact with a cooling medium, said tubular conduit in communication with said first separation mans (c);

(e) conduit means connecting said tubular conduit (d) and said first separation means (c) for passing said first overhead gaseous stream from said first separation means through said tubular conduit (d) whereby said first overhead gaseous stream is cooled and at least a portion of diamondoid compounds contained in said first overhead gaseous stream is precipitated;

(f) conduit means in communication with said tubular conduit means (e) for withdrawing a chilled stream from said tubular conduit means (e);

(g) second means connected to said conduit means (f) for receiving said chilled stream and for separating liquid components from said chilled stream to provide a second overhead gaseous stream substantially free of liquid and a second liquid bottom stream;

(h) a sorption vessel in valved communication with said second separation means (g) for contacting said second overhead gaseous stream with a sorbent in said sorption vessel for a period of time sufficient for said sorbent to remove substantially all diamondoid compounds remaining in said second overhead gaseous stream;

(i) conduit means for withdrawing a stream of substantially dry hydrocarbon gas from said sorption vessel;

(j) a first vessel downstream from and in communication with said first separations means (c) for collecting said first liquid bottom stream from said first separation means (c);

(k) a second vessel in valved communication with said second separation means (g) for collecting said second liquid bottom stream from said second separation means (g);

(l) means for monitoring the pressure drop across said tubular conduit (d);

(m) means for monitoring the pressure drop across said sorption vessel (h); and (n) valve means located in a conduit connecting said sampling means (a) with said depressuring and heating means (b) for interrupting the flow of said gaseous hydrocarbon sample stream when said pressure drop across either of said tubular conduit (d) or said sorption vessel (h) indicate plugging.

* * * * *

UNITED STATES PATENT AND TRADEMARK OFFICE
CERTIFICATE OF CORRECTION

PATENT NO. : 5,126,274

DATED : June 30, 1992

INVENTOR(S) : G. E. McIver and R. E. Roach

It is certified that error appears in the above-identified patent and that said Letters Patent is hereby corrected as shown below:

Column 9:
In claim 9, line 12 "depressing" should read "depressuring"

Signed and Sealed this

Seventh Day of September, 1993

Attest:

BRUCE LEHMAN

Attesting Officer

Commissioner of Patents and Trademarks